US010106570B2

(12) United States Patent
Adam et al.

(10) Patent No.: US 10,106,570 B2
(45) Date of Patent: Oct. 23, 2018

(54) EDIBLE PLASTICIZERS FOR FOOD AND FOOD PACKAGING FILMS

(71) Applicant: EMPIRE TECHNOLOGY DEVELOPMENT LLC, Wilmington, DE (US)

(72) Inventors: Georgius Abidal Adam, Edensor Park (AU); Anita Needham, Mangerton (AU)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 70 days.

(21) Appl. No.: 14/901,696

(22) PCT Filed: Jun. 28, 2013

(86) PCT No.: PCT/US2013/048604
§ 371 (c)(1),
(2) Date: Dec. 28, 2015

(87) PCT Pub. No.: WO2014/209369
PCT Pub. Date: Dec. 31, 2014

(65) Prior Publication Data
US 2016/0145288 A1 May 26, 2016

(51) Int. Cl.
C07C 67/08 (2006.01)
C07C 69/017 (2006.01)
C07C 69/76 (2006.01)
C07H 15/18 (2006.01)
A23G 4/06 (2006.01)
A23L 29/00 (2016.01)
A23L 7/126 (2016.01)
A23L 13/40 (2016.01)
C08K 5/134 (2006.01)
C08K 5/1535 (2006.01)
C08K 5/1545 (2006.01)

(52) U.S. Cl.
CPC .............. C07H 15/18 (2013.01); A23G 4/06 (2013.01); A23L 7/126 (2016.08); A23L 13/42 (2016.08); A23L 29/035 (2016.08); C07C 67/08 (2013.01); C07C 69/017 (2013.01); C07C 69/76 (2013.01); C08K 5/134 (2013.01); C08K 5/1535 (2013.01); C08K 5/1545 (2013.01); A23V 2002/00 (2013.01)

(58) Field of Classification Search
None
See application file for complete search history.

(56) References Cited

U.S. PATENT DOCUMENTS

| | | |
|---|---|---|
| 2,586,274 A | 2/1952 | Tollenaar |
| 4,280,008 A | 7/1981 | Schoellkopf et al. |
| 4,401,754 A | 8/1983 | Suzuki et al. |
| 4,489,155 A | 12/1984 | Sakanoue et al. |
| 4,671,883 A | 6/1987 | Connell et al. |
| 4,739,097 A | 4/1988 | Sander et al. |
| 4,912,256 A | 3/1990 | Cronje |
| 5,034,045 A | 7/1991 | Alexander |
| 5,362,615 A | 11/1994 | Hagemann et al. |
| 5,463,129 A | 10/1995 | Lysenko et al. |
| 6,297,396 B1 | 10/2001 | Sas et al. |
| 6,569,900 B1 | 5/2003 | Dekker et al. |
| 7,192,455 B2 | 3/2007 | Plos et al. |
| 8,211,558 B2 | 7/2012 | Yoshimura |
| 2004/0115334 A1 | 6/2004 | Romero Olmedo |
| 2004/0224844 A1 | 11/2004 | Bickers et al. |
| 2005/0069974 A1 | 3/2005 | Gladkov et al. |
| 2006/0058566 A1 | 3/2006 | Shulgin et al. |
| 2006/0286046 A1 | 12/2006 | Haber |
| 2007/0212434 A1 | 9/2007 | Day et al. |
| 2009/0110802 A1 | 4/2009 | Pibarot et al. |
| 2009/0306361 A1 | 12/2009 | Kawabe et al. |
| 2010/0035887 A1 | 2/2010 | Ricciardi |
| 2010/0119653 A1 | 5/2010 | Hall |
| 2011/0031188 A1 | 2/2011 | Perminova et al. |
| 2011/0111066 A1 | 5/2011 | Ferguson et al. |
| 2012/0149697 A1 | 6/2012 | Legname et al. |
| 2012/0213756 A1 | 8/2012 | Petralia |
| 2012/0220752 A1 | 8/2012 | Schutt |
| 2016/0108010 A1 | 4/2016 | Adam et al. |

FOREIGN PATENT DOCUMENTS

| | | |
|---|---|---|
| CN | 102432306 A | 5/2012 |
| CN | 102863687 A | 1/2013 |
| DE | 2658941 A1 | 7/1978 |
| EP | 0203607 A1 | 12/1986 |
| JP | 558173138 A | 10/1983 |
| JP | 6145697 A | 5/1994 |
| JP | H06211746 A | 8/1994 |

(Continued)

OTHER PUBLICATIONS

Danjo, JP 08188553, Jul. 23, 1996, CAPLUS record.*
Chen, Langmuir 2005, 21, 10931-10940. (Year: 2005).*
"BHT Product Description," Wholesale Nutrition, accessed at https://web.archive.org/web/20130509093835/http://www.nutri.com/index.cfm/product/31_17/bht.cfm accessed on Mar. 15.
"BioAg Fulvic & Humic Solutions ," accessed at https://web.archive.org/web/20120621081858/http://www.bioag.com/teamfulvic/fulvicresearch.html accessed on Mar. 15, 2016, pp. 2.
"Folic acid fact sheet," epublications accessed at https://web.archive.org/web/20130429034307/http://www.womenshealth.gov/publications/our-publications/fact-sheet/folic-acid.html content last updated Jul. 16, 2012, pp. 6.

(Continued)

Primary Examiner — Layla D Berry

(57) ABSTRACT

Disclosed are plasticizers, salts thereof, chelates thereof and cleavage derivatives thereof, that exhibit a superior combination of properties. The plasticizers can be used for a variety of purposes, including food preparation, cosmetics, beverages and polymeric matrices. The plasticizers can be prepared by esterifying gallic acid, fulvic acid, or tannic acid.

15 Claims, No Drawings

(56) References Cited

FOREIGN PATENT DOCUMENTS

| | | |
|---|---|---|
| JP | H06222553 A | 8/1994 |
| JP | H07330669 A | 12/1995 |
| JP | H09227450 A | 9/1997 |
| JP | 2000086579 A | 3/2000 |
| JP | 2003049196 A | 2/2003 |
| JP | 2004352973 A | 12/2004 |
| JP | 2005272471 A | 10/2005 |
| JP | 2006328298 A | 12/2006 |
| JP | 2009298727 A | 12/2009 |
| WO | 9531192 A1 | 11/1995 |
| WO | 9925191 A1 | 5/1999 |
| WO | 3965702 A1 | 12/1999 |
| WO | 2001034094 A2 | 5/2001 |
| WO | 2005118511 A2 | 12/2005 |
| WO | 2011028495 A1 | 3/2011 |
| WO | 2014193337 A1 | 12/2014 |

OTHER PUBLICATIONS

"Fulvic Acid a Substance Critical to Human Health," accessed at http://web.archive.org/web/20110910224221/http://www.realrawfood.com/sites/default/files/article/Fulvic%20Acid%20Report.pdf accessed on Dec. 11, 2015, pp. 48.

"Fulvic Acid Benefits," accessed at https://web.archive.org/web/20130525140616/http://www.supremefulvic.com/documents/html/fulvic_acid.php, accessed on Mar. 15, 2016, pp. 22.

"Fulvic acid," Encyclopedia Britannica accessed at http://www.britannica.com/science/fulvic-acid accessed on Mar. 15, 2016, pp. 2.

"Global Trends in Polymer Additives," accessed at http://www.plastemart.com/Plastic-Technical-Article.asp?LiteratureID=1514&Paper=global-trends-in-polymer-additives, Oct. 29, 2010, pp. 2.

"How You Rot & Rust," accessed at https://web.archive.org/web/20130302050256/http://biomedx.com/microscopes/rrintro/rr1.html, accessed on Mar. 15, 2016, pp. 1.

"Humic & Fulvic Acids:The Black Gold of Agriculture," accessed at http://web.archive.org/web/20120417060303/http://www.humintech.com/pdf/humicfulvicacids.pdf accessed on Mar. 15, 2016, pp. 10.

"Humic & Fulvic Substances I," Supremefulvic.com accessed at http://www.supremefulvic.com/documents/pdf/2.about.humic-fulvic.substances.1.pdf, accessed on Mar. 15, 2016, pp. 35.

"Humic & Fulvic Substances II," Supremefulvic.com accessed at http://www.supremefulvic.com/documents/pdf/2.about.humic-fulvic.substances.1.pdf, accessed on Mar. 15, 2016, pp. 38.

"Investigation of humic acid N with X-ray photoelectron spectroscopy: Effect of acid hydrolysis an comparison with 15N cross polarization/ magic angle spinning nuclear magnetic resonance spectroscopy," International Atomic energy Agency, Technical Report Series, International Atomic Energy Agency, Vienna, vol. 47, No. 4, p. 263 (Jul. 2006).

"It's Perfectly Clear The Case Against PVC Packaging," Masspirg, accessed at https://web.archive.org/web/20050305121509/http://www.pirg.org/masspirg/enviro/sw/pvc/, accessed on Mar. 15, 2016, pp. 2.

"List of food additives," accessed at http://web.archive.org/web/20130424122000/http://en.wikipedia.org/wiki/List_of_food_additives last modified on Mar. 3, 2013, pp. 15.

"pH and Acidosis," Supremefulvic.com accessed at https://web.archive.org/web/20090922095505/http://www.supremefulvic.com/documents/html/pHbyDrLam.html, accessed on Mar. 15, 2016, pp. 5.

"pH and cancer," accessed at http://www.supremefulvic.com/documents/pdf/11.ph.and.cancer.pdf, accessed on Mar. 15, 2016, pp. 3.

"Root of All Disease," Supremefulvic.com accessed at http://www.supremefulvic.com/documents/pdf/7.the.root.of.all.disease(edited).pdf, accessed on Mar. 15, 2016, pp. 19.

"The pH Regularatory System of the Body," accessed at http://www.supremefulvic.com/documents/pdf/10.how.you.rot.and.rust.pdf, accessed on Mar. 15, 2016, pp. 28.

"Vitamin C in Food Processing," accessed at http://web.archive.org/web/20120916175528/http://www.mratcliffe.com/images/vcb.pdf accessed on Mar. 15, 2016, pp. 5.

"What Is Fulvic Acid?" Supremefulvic.com accessed at https://web.archive.org/web/20150319160405/http://www.supremefulvic.com/documents/pdf/1.what.is.fulvic.acid.pdf accessed on Mar. 15, 2016, pp. 17.

Adam, G.A., et al., "Humic substances as new stabilisers for polyvinylchloride," Thermochima Acta, vol. 99, pp. 217-222 (Mar. 1, 1986).

Aeschbacher, M. et al., "Antioxidant properties of humic substance," Environmental Science and Technology, vol. 46, No. 9, pp. 4916-4925 (Jan. 1, 2012).

Aguilar, F., et al., "Chromium(III)-, iron(II)- and selenium-humic acid/fulvic acid chelate and supplemented humifulvate added for nutritional purposes to food supplements," The EFSA Journal, vol. 1147, pp. 1-36, (Jun. 5, 2009).

Alvarez-Puebla, R.A., et al., "Theoretical study on fulvic acid structure, conformation and aggregation: A molecular modelling approach," Science of the Total Environment ,vol. 358,Issue. 1-3, pp. 243-254 , (Apr. 1, 2006).

Atalay, Y.B., et al., "Distribution of Proton Dissociation Constants for Model Humic and Fulvic Acid Molecules," Environmental Science & Technology, vol. 43, Issue. 10, pp. 3626-3631, (Apr. 17, 2009).

Avvakumova, N.P., et al., "Antioxidant Properties of Humic Substances Isolated Form Peloids," Pharmaceutical Chemistry Journal, vol. 45, No. 3, pp. 192-193 (Mar. 2011).

Babler, J.H., et al., "Reductive cleavage versus hydrogenation of allyl aryl ethers and allylic esters using sodium borohydride/catalytic ruthenium(III) in various aqueous solvent mixtures," Tetrahedron Letters, vol. 52, Issue 7, pp. 745-748 (Feb. 16, 2011).

Badary, O.A., et al., "Thymoquinone is a potent superoxide anion scavenger," Drug & Chemical Toxicology, vol. 26, No. 2, pp. 87-98 (May 2003).

Bernard, A.M., et al., "Dealkylation of Activated Alkyl Aryl Ethers Using Lithium Chloride in Dimethylformamide" Synthesis, vol. 1989, Issue 4, pp. 287-289 (Apr. 1989).

Bisig, M.D., "Plasticizer Market Update," BASF Corporation, Jul. 19-21, 2009, pp. 20.

D'Arcgivio M., et al., "Polyphenols, dietary sources and bioavailablility," Ann 1st Super Sanita, vol. 43, No. 4, pp. 348-361 (2007).

Densley, B., "Plasticisers in our food &&," Green Left, accessed at https://web.archive.org/web/20101108234729/http://www.greenleft.org.au/node/11274, Aug. 14, 1996, pp. 2.

Duffus, J.H., "Heavy-metals—A meaningless term," Chemistry and Human Health Division Clinical Chemistry Section, Commission on Toxicology, vol. 74, No. 5, pp. 793-807 (2002).

Extended European Search Report for European Application No. 13885836.0 dated Feb. 17, 2016, pp. 8.

Fang, Z., et al., "Lithium chloride-catalyzed selective demethylation of aryl methyl ethers under microwave irradiation," Journal of Molecular Catalysis A: Chemical, vol. 274, Issues 1-2, p. 16-23 (Sep. 3, 2007).

Faust, R.H., "Fulvic acid solution WuJinSan crucial cellular antioxidant," pp. 3 (2006).

Food poisoning, accessed at http://web.archive.org/web/20120925125222/http://www.markusrothkranz.com/freebies/podpoisoning.pdf, accessed on Mar. 5, 2016, pp. 7.

Giovanela, M., et al., "Elemental compositions FT-IR spectra and thermal behavior of sedimentary fulvic and humic acids from aquatic and terrestrial environments," Geochemical Journal , vol. 38, Issue 3, pp. 255-264 (2004).

Gregor, J.E., and Powell, H.K.J., "Effects of Extraction Procedures on Fulvic Acid Properties," Science of the total Environment , vol. 62, pp. 3-12 (1987).

Hua, Li, "Development and Application of Peat Humic Acid in Plastics Industry," HeBei Chemical Engineering, vol. 2, pp. 47-48 (1990).

International Search Report and Written Opinion for International Application No. PCT/US2013/037144 dated Nov. 5, 2013, pp. 13.

International Search Report and Written Opinion for International Application No. PCT/US2013/042807 dated Jan. 24, 2014, pp. 11.

(56) References Cited

OTHER PUBLICATIONS

International Search Report and Written Opinion for International Application No. PCT/US2013/042814 dated Jan. 31, 2014, pp. 11.
Käcker, T., et al., "Structural characterisation of humic acid-bound PAH residues in soil by 13C-CPMAS-NMR-spectroscopy: evidence of covalent bonds," Chemosphere, vol. 48, Issue 1, pp. 117-131 (2002).
Kiprop, A., et al., "Synthesis of Humic and Fulvic Acids and their Characterization using Optical Spectroscopy (ATR-FTIF and UV-Visible)," International Journal of Applied Science and Technology, vol. 3, Issue. 8, pp. 28-35 (Dec. 1, 2013).
Klocking, R., and Helbig, B., "Medical aspects and applications of Humic substances" accessed at http://www.supremefulvic.com/documents/pdf/5.medical.aspects.and.applications.of.humic.substances.pdf, accessed on Mar. 15, 2016, pp. 2.
Kucerik, J., et al., "Antioxidant effect of lignite humic acids and its salts on the thermo-oxidative stability/degradation of polyvinyl alcohol blends," Environmental Chemistry Letters, vol. 6, Issue 4, pp. 241-245 (Nov. 2008).
Leenheer, J.A., et al., "Molecular Resolution and Fragmentation of Fulvic Acid by Electrospray Ionization/Multistage Tandem Mass Spectrometry," Analytical Chemistry, vol. 73, Issue 7, pp. 1461-1471 (Mar. 7, 2001).
Manach, C., et al., "Polyphenols: food sources and bioavailability1,2," American Journal of Clinical Nutrition, vol. 79, No. 5, pp. 727-747 (May 2004).
Marton, J., and Alder, E., "Carbonyl Groups in Lignin. III. Mild Catalytic Hydrogenation of Björkman Lignin," Acta Chemica Scandinavica, vol. 15, No. 2, pp. 370-83 (1961).
Okubo, T., et al., "Cell death induced by the phenolic antioxidant tert-butylhydroquinone and its metabolite tert-butylquinone in human monocytic leukemia u937 cells," Food and Chemical toxicology, vol. 41, Issue 5, pp. 679-688 (May 2003).
Pena-Mendez, E.M, et al., "Humic substances-compounds of still unknown structure: applications in agriculture, industry, environment, and biomedicine," Journal of Applied Biomedicine., vol. 3, No. 1, pp. 13-24 (Nov. 22, 2004).
Peng et al., Production of Plastics by Regeneration of Humic Acid through Coal Nitration, Chinese Coal, vol. 25 Issue. 4, pp. 39-40, (1999).
Pettit, R.E.,"Organic Matter, Humus, Humate, Humic Acid, Fulvic Acid and Humin: Their Importance in Soil Fertility and Plant Health," accessed at http://www.humates.com/pdf/ORGANICMATTERPettit.pdf, accessed on Mar. 15, 2016, pp. 17.
Rath, N.C., et al., "Effects of humic acid on broiler chickens," Poultry Science, vol. 85, Issue 3, pp. 410-414 (Mar. 2006).
Rodriguez, N.C., et al., "Antioxidant activity of fulvic acid: A living matter-derived bioactive compound," Journal of Food, Agriculture & Environment, vol. 9, Issue 3-4, pp. 123-127 (Jul. 1, 2011).
Safer, A.M., and Al-Nughamish, A.J., "Heptatoxicity induced by the anti-oxidant food additive, butylated hydroxytoluene (BHT), in rates: An electron microscopical study" Histology and Histopatholgly, vol. 14, Issue 2, pp. 391-406 (Apr. 1999).
Sarafian, T. A., et al., "Synergistic cytotoxicity of ∆9 tetrahydrocannabinol and butylated hydroxyanisole," Toxicology Letters, vol. 133, pp. 171-179 (Jul. 21, 2002).
Schepetkin, I.A., et al., "Characterization and Biological Activities of Humic Substances from Mumie," J Agric Food Chem., vol. 51, No. 18, pp. 5245-5254 (Aug. 2003).
Schneider, J., et al., "Inhibition of HIV-1 in Cell Culture by Synthetic Humate Analogues Derived from Hydroquinone : Mechanism of Inhibition," US National Library of Medicine National Institutes of HealthSearch database, vol. 218, No. 2, pp. 389-395 (Apr. 15, 1996).
Sonnenberg, L.B., et al., "Chemical Degradation of Humic Substances for Structural Characterization," in Aquatic Humic Substances, Chapter 1, Advances in Chemistry, vol. 219, pp. 3-23 (Dec. 15, 1988).
Supplementary European Search Report for European Application No. 13885964.0 dated Feb. 10, 2016, pp. 6.
Supplementary European Search Report for European Application No. 13882133.5 dated Nov. 10, 2016, pp. 9.
Supplementary European Search Report for European Application No. 13888488.7 dated Jan. 10, 2017, pp. 8.
Verhagen, H., et al., "Butylated hydroxyanisole in perspective," Chemico-Biological Interactions, vol. 80, Issue 2, pp. 109-134 (1991).
Willard, P.G., and Fryhle, C.B., et al., "Boron trihalide-methyl sulfide complexes as convenient reagents for dealkylation of aryl ethers," Tetrahedron Letters, vol. 21, Issue 39, pp. 3731-3734 (1980).
Zhipei, "Plastic Additive," Jian Xi Humic Acid, pp. 1-66 (1985).
6 Food Ingredient Mega Trends, Natural Products Insider, accessed at http://www.naturalproductsinsider.com/news/2010/09/6-food-ingredient-mega-trends.aspx, Sep. 30, 2010, pp. 3.
Fulvic acid Chemical compound, Encyclopedia Britannica, accessed at http://www.britannica.com/science/fulvic-acid, accessed on Mar. 4, 2016, pp. 2.
Fulvic Acid the Miracle Molecule, Supreme Fulvic LLC, accessed at https://web.archive.org/web/20120329231513/http://www.supremefulvic.com/documents/pdf/8.fulvic.acid.report.pdf, accessed on Mar. 4, 2016, pp. 1-42.
Gallates (Propyl, Octyl and Dodecyl), Inchem, accessed at https://web.archive.org/web/20130619094846/http://www.inchem.org/documents/jecfa/jecmono/v32je02.htm, accessed on Mar. 4, 2016, pp. 16.
Presenting BioVinyl, BioVinyl, accessed at http://www.biovinyl.com/, accessed on Mar. 4, 2016, p. 2.
Tannins derivates, Ajinomoto, accessed at https://web.archive.org/web/20120318055927/http://www.natural-specialities.com/natural-specialities/en/8457-tannins-derivates.html, accessed on Mar. 4, 2016, pp. 1.
International Search Report and Written Opinion for International Application No. PCT/US2013/048604 dated Feb. 25, 2014.
Kohut-Svelko et al., Overview of the preparation of pure polyaniline and conductive composites in dispersed media and by thermal processes: from laboratory to semi-industrial scale, Polymer international (Oct. 2006), 55(10) pp. 1184-1190.
Lundin et al., Understanding food structure and function in developing food for appetite control, Nutrition and Dietetics (Jun. 2008), 65(S3) pp. S79-S85.
Reische et al., Antioxidants, in Food Lipids Chemistry, Nutrition, and Biotechnology, Chapter 15, Akoh and Min eds. (2002), pp. 30.
Shahidi, Antioxidants in food and food antioxidants, Food / Nahrung (May 1, 2000), 44(3) pp. 158-163.
Shahidi, Antioxidants, in Food Additive Databook, Blackwell Science (2003), Smith and Hong-Shum, pp. 75-83.
Shahidi and Zhong, Antioxidants Regulatory Status, Bailey's Industrial Oil and Fat Products, Sixth Edition (2005), Chapter 12, pp. 491-512.
Liao et al., Structural Characterization of Aquatic Humic Material, Environmental Science and Technology (Jul. 1982), 16(7):403-410.

\* cited by examiner

EDIBLE PLASTICIZERS FOR FOOD AND FOOD PACKAGING FILMS

CROSS-REFERENCE TO RELATED APPLICATION

This patent application is a U.S. National Stage filing under 35 U.S.C. § 371 of International Patent Application No. PCT/US2013/048604, filed on Jun. 28, 2013, and entitled "EDIBLE PLASTICIZERS FOR FOOD AND FOOD PACKAGING FILMS," which is incorporated herein by reference in its entirety.

BACKGROUND

Various types of antioxidant additives are used to protect food from oxidation. Soluble vitamin C (ascorbic acid and its salts) is employed to protect some fruits and meat. Ascorbyl stearate and ascorbyl palmitate as oil-soluble or fat-soluble antioxidants are sometimes employed with other foods. Currently used antioxidants include BHT (butylated hydroxytoluene), TBHQ (t-butyl hydroquinone), BHA (butylated hydroxy anisole), gallic acid, and gallic esters.

Some natural antioxidants, such as vitamins, minerals, and enzymes are also regarded as nutrients due to their bioactivity. Ascorbic acid (Vitamin C) and tocopherols (a class of compounds with Vitamin E activity) are the most important commercial natural antioxidants but they can be expensive and unstable in processing and storage at high temperatures.

Consumer interest in and awareness of the health properties of food plasticizers has also been increasing in recent years. This has simultaneously increased global sales of food plasticizers and foods that are recognized as being naturally rich in antioxidants. As the sector develops, food plasticizers are now being used in the manufacture of a greater variety of foods.

SUMMARY

Disclosed are plasticizing compositions including at least one compound of formula I, formula II, or formula III, a salt thereof, chelate thereof, or combination thereof, wherein $R^{1A}$, $R^{1B}$, and $R^{1C}$ are independently selected from hydrogen, $-(C=O)-(C_8-C_{16})$alkyl, or $-(C=O)-(C_8-C_{16})$alkenyl; $R^2$ is hydrogen, $-(C_8-C_{16})$alkyl, $-(C_8-C_{16})$alkenyl, -mannitosyl, -sorbitolyl, or -sucrosyl; wherein at least one of $R^{1A}$, $R^{1B}$, $R^{1C}$, and $R^2$ are not hydrogen; each $R^3$ is independently selected from hydrogen, $-(C_2-C_{16})$alkyl, $-(C_2-C_{16})$alkenyl, -mannitosyl, -sorbitolyl, or -sucrosyl; wherein at least one of $R^3$ is not hydrogen; and each $R^4$ is independently selected from hydrogen, $-(C=O)-(C_8-C_{14})$alkyl, $-(C=O)-(C_8-C_{14})$alkenyl, each $R^4$ may be the same or different; wherein at least one of $R^4$ is not hydrogen.

Also disclosed are methods of preparing a plasticizing compound, the methods including esterifying at least one of gallic acid, fulvic acid, and tannic acid groups to form at least one plasticizing compound of formula I, formula II, or formula III, a salt thereof, a chelate thereof, or combination thereof, wherein at least one of $R^{1A}$, $R^{1B}$, $R^{1C}$, and $R^2$ are not hydrogen; each $R^3$ is independently selected from hydrogen, $-(C_2-C_{16})$alkyl, $-(C_2-C_{16})$alkenyl, -mannitosyl, -sorbitolyl, or -sucrosyl; wherein at least one of $R^3$ is not hydrogen; and each $R^4$ is independently selected from hydrogen, $-(C=O)-(C_8-C_{16})$alkyl, and $-(C=O-(C_8-C_{16})$alkenyl, each $R^4$ may be the same or different; wherein at least one of $R^4$ is not hydrogen.

Further disclosed are treated food products including at least one plasticizing compound of formula I, formula II, or formula III, or a salt thereof, or chelate thereof, wherein $R^{1A}$, $R^{1B}$, and $R^{1C}$ are independently selected from hydrogen, $-(C=O)-(C_8-C_{16})$alkyl, and $-(C=O)-(C_8-C_{16})$alkenyl; $R^2$ is hydrogen, $-(C_8-C_{16})$alkyl, $-(C_8-C_{16})$alkenyl, -mannitosyl, -sorbitolyl, or -sucrosyl; wherein at least one of $R^{1A}$, $R^{1B}$, $R^{1C}$, and $R^2$ are not hydrogen; each $R^3$ is independently selected from hydrogen, $-(C_2-C_{16})$alkyl, $-(C_2-C_{16})$alkenyl, -mannitosyl, -sorbitolyl, and -sucrosyl; wherein at least one of $R^3$ is not hydrogen; and each $R^4$ is independently selected from hydrogen, $-(C=O)-(C_8-C_{16})$alkyl, and $-(C=O)-(C_8-C_{16})$alkenyl, wherein at least one of $R^4$ on each ring B, C, D, E, and F is not hydrogen; in a food product.

DETAILED DESCRIPTION

The above summary of the present technology is not intended to describe each illustrated embodiment or every possible implementation of the present technology. The detailed description, which follows, particularly exemplifies these embodiments.

Before the present compositions and methods are described, it is to be understood that they are not limited to the particular compositions, methodologies or protocols described, as these may vary. It is also to be understood that the terminology used in the description is for the purpose of describing the particular versions or embodiments only, and is not intended to limit their scope which will be limited only by the appended claims.

Compounds based on ester derivatives of gallic acid, fulvic acid, and tannic acid, their salts and chelates are described herein. The compounds may have antioxidant properties. The compounds, their salts, and their chelates can be useful for stabilizing foods, cosmetics, beverages and nutritional supplements. The compounds can be prepared from the three acids by esterification under controlled conditions. In certain embodiments the antioxidation efficiency of such sustainable natural derivatives is due to their chemical structure which contains functional groups that are known as antioxidants and free radical scavenger active groups.

Gallic acid has three phenolic sites ($R^{1A}$, $R^{1B}$, $R^{1C}$) and a carboxylic acid site ($R^2$) for possible esterification or formation of metal chelates. When $R^{1A}$, $R^{1B}$, $R^{1C}$, and $R^2$ are each H in the chemical structure (I), the compound is gallic acid. In an embodiment, structure (I) provides ester derivatives of gallic acid, wherein $R^{1A}$, $R^{1B}$, and $R^{1C}$ are independently selected from hydrogen, $-(C=O)-(C_8-C_{16})$alkyl, or $-(C=O)-(C_8-C_{16})$alkenyl, $R^2$ is hydrogen, $-(C_8-C_{16})$alkyl, $-(C_8-C_{16})$alkenyl, -mannitosyl, -sorbitolyl, or -sucrosyl, and wherein at least one of $R^{1A}$, $R^{1B}$, $R^{1C}$, and $R^2$ are not hydrogen. In some embodiments, all of $R^{1A}$, $R^{1B}$, $R^{1C}$, and $R^2$ are not hydrogen. In each of the various embodiments, alkyl or alkenyl may be substituted with a sugar, for example mannitosyl, sorbitolyl, or sucrosyl, or with an amino acid.

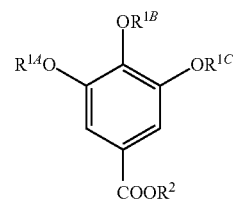

I

Fulvic acid has six carboxylic acid sites ($R^3$) for possible esterification or formation of metal chelates. When each of $R^3$ is H, the chemical structure (II) is fulvic acid. In an embodiment, structure (II) provides an ester derivative of fulvic acid, wherein each $R^3$ is independently selected from hydrogen, —($C_2$-$C_{16}$)alkyl, —($C_2$-$C_{16}$)alkenyl, -mannitosyl, -sorbitolyl, or -sucrosyl, and wherein at least one $R^3$ is not hydrogen. In some embodiments, all $R^3$ in chemical structure (II) are not hydrogen. In each of the various embodiments, alkyl or alkenyl may be substituted with a sugar, for example mannitosyl, sorbitolyl, or sucrosyl, or with an amino acid.

II

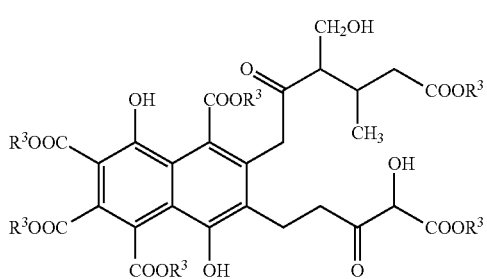

Tannins are weak acids having fifteen phenolic sites for possible esterification or formation of metal chelates. When each $R^4$ is H, the chemical structure (III) is an exemplary tannin. In an embodiment, structure III provides an ester derivative of a tannin, wherein each $R^4$ is independently selected from hydrogen, —(C═O)—($C_8$-$C_{16}$)alkyl, —(C═O)—($C_8$-$C_{16}$)alkenyl, each $R^4$ may be the same or different, and wherein at least one of $R^4$ is not hydrogen. In some embodiments, all of $R^4$ in chemical structure (III) are not hydrogen. In each of the various embodiments, alkyl or alkenyl may be substituted with a sugar, for example mannitosyl, sorbitolyl, or sucrosyl, or with an amino acid.

III

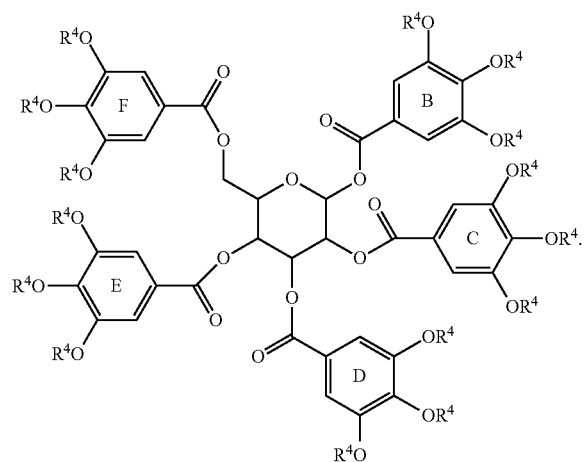

The ester derivatives of the structures I-III have various uses including use as a plasticizer, such as for example food plasticizers. These plasticizers can be, for example, a viscous liquid, a solution, or chelated with transition (nutrient) metals. Any free carboxylic acid group or phenolic group of the described embodiments can be transformed into carboxylate salts or phenylates of Na, K, Ca, Zn, Mg, and can form chelates with divalent and trivalent metal ions.

The plasticizers of various embodiments do not require purification steps, such as ultrafiltration or desalination, nor fractionation into fractions with distinct molecular weights and high purity. However, such steps may be employed advantageously.

The ester derivatives of the structures I-III may provide a stabilizing effect at various doses in foods. The antioxidant property of the crude extract of the ester derivatives described herein may allow its usage at a low concentration, hence, avoiding any undesired color or flavor effect that might arise from the use of the ester derivatives of the structures I-III as a food plasticizer.

A plasticizing composition may include at least one compound of formula I, formula II, or formula III, a salt thereof, chelate thereof, or combination thereof, wherein $R^{1A}$, $R^{1B}$, and $R^{1C}$ are independently selected from hydrogen, —(C═O)—($C_8$-$C_{16}$)alkyl, or —(C═O)—($C_8$-$C_{16}$)alkenyl; $R^2$ is hydrogen, —($C_8$-$C_{16}$)alkyl, —($C_8$-$C_{16}$)alkenyl, -mannitosyl, -sorbitolyl, or -sucrosyl; wherein at least one of $R^{1A}$, $R^{1B}$, $R^{1C}$, and $R^2$ are not hydrogen; each $R^3$ is independently selected from hydrogen, —($C_2$-$C_{16}$)alkyl, —($C_2$-$C_{16}$)alkenyl, -mannitosyl, -sorbitolyl, or -sucrosyl, and wherein at least one $R^3$ is not hydrogen; and each $R^4$ is independently selected from hydrogen, —(C═O)—($C_8$-$C_{16}$)alkyl, —(C═O)—($C_8$-$C_{16}$)alkenyl, each $R^4$ may be the same or different; wherein at least one $R^4$ is not hydrogen. In some embodiments, all $R^4$ are not hydrogen. In each of the various embodiments, alkyl or alkenyl may be substituted with a sugar, for example mannitosyl, sorbitolyl, or sucrosyl, or with an amino acid.

In one embodiment, a composition may include at least one compound of formula I, a salt thereof, or chelate thereof, wherein $R^{1A}$, $R^{1B}$, and $R^{1C}$ are independently selected from hydrogen, —(C═O)—($C_8$-$C_{16}$)alkyl, or —(C═O)—($C_8$-$C_{16}$)alkenyl; $R^2$ is hydrogen, —($C_8$-$C_{16}$)alkyl, —($C_8$-$C_{16}$)alkenyl, -mannitosyl, -sorbitolyl, or -sucrosyl; wherein at least one of $R^{1A}$, $R^{1B}$, $R^{1C}$, and $R^2$ are not hydrogen. In another embodiment, a composition may include at least one compound of formula I, wherein $R^{1A}$, $R^{1B}$, and $R^{1C}$ are independently selected from hydrogen, —(C═O)—($C_8$-$C_{16}$)alkyl, or —(C═O)—($C_8$-$C_{16}$)alkenyl; having $R^2$ is —($C_8$-$C_{16}$)alkyl, or —($C_8$-$C_{16}$)alkenyl; and wherein at least one of $R^{1A}$, $R^{1B}$, and $R^{1C}$ is not hydrogen. In still another embodiment, a composition may include at least one compound of formula I, wherein $R^{1A}$, $R^{1B}$, and $R^{1C}$ are independently selected from hydrogen, —(C═O)—($C_8$-$C_{16}$) alkyl, or —(C═O)—($C_8$-$C_{16}$)alkenyl, $R^2$ is -mannitosyl, -sorbitolyl, or -sucrosyl; and wherein at least one of $R^{1A}$, $R^{1B}$, and $R^{1C}$ is not hydrogen. In yet another embodiment, a composition may include at least one compound of formula I, wherein $R^{1A}$, $R^{1B}$, and $R^{1C}$ are independently selected from hydrogen, —(C═O)—($C_8$-$C_{16}$)alkyl, or —(C═O)— ($C_8$-$C_{16}$)alkenyl, wherein $R^2$ is selected from:

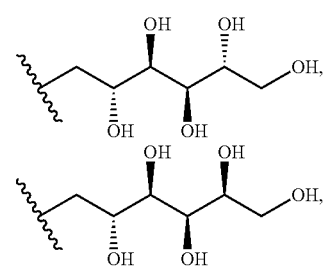

-continued

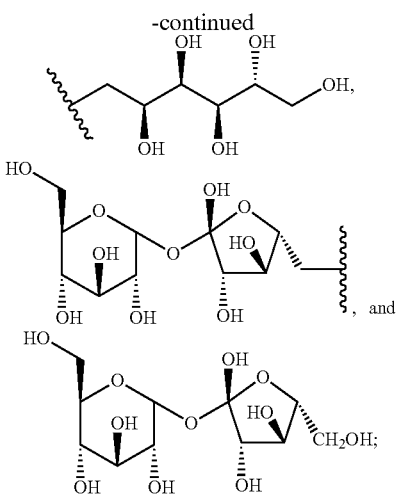

and
wherein at least one of $R^{1A}$, $R^{1B}$, and $R^{1C}$ is not hydrogen. In some embodiments, all of $R^{1A}$, $R^{1B}$, and $R^{1C}$ are not hydrogen. In each of the various embodiments, alkyl or alkenyl may be substituted with an amino acid or a sugar such as, for example, mannitosyl, sorbitolyl, or sucrosyl.

In still another embodiment, a composition may include at least one compound of formula I, wherein $R^{1A}$, $R^{1B}$, and $R^{1C}$ are independently selected from hydrogen, —(C=O)—($C_8$-$C_{16}$)alkyl, or —(C=O)—($C_8$-$C_{16}$)alkenyl, wherein $R^2$ is selected from

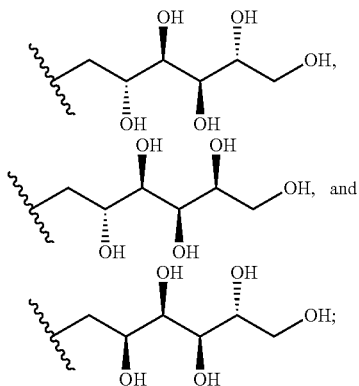

and wherein at least one of $R^{1A}$, $R^{1B}$, and $R^{1C}$ is not hydrogen. In another embodiment, $R^{1A}$, $R^{1B}$, and $R^{1C}$ are independently selected from —(C=O)—($C_8$-$C_{16}$)alkyl, and —(C=O)—($C_8$-$C_{16}$)alkenyl, $R^2$ is hydrogen, —($C_8$-$C_{16}$)alkyl, —($C_8$-$C_{16}$)alkenyl, -mannitosyl, -sorbitolyl, or -sucrosyl; wherein at least one of $R^{1A}$, $R^{1B}$, $R^{1C}$, and $R^2$ are not hydrogen. In some embodiments, all of $R^{1A}$, $R^{1B}$, $R^{1C}$, and $R^2$ are not hydrogen. In each of the various embodiments, alkyl or alkenyl may be substituted with an amino acid or a sugar such as, for example, mannitosyl, sorbitolyl, or sucrosyl. In an embodiment, the compositions disclosed herein may include at least one compound of formula I wherein the compound is a salt thereof, or chelate thereof. In an embodiment, the compositions disclosed herein may include at least one compound of formula I wherein the compound is a sodium salt, ammonium salt, potassium salt, calcium salt, magnesium salt, manganese salt, zinc salt, iron salt, or a combination thereof. In an embodiment, the compositions disclosed herein may include at least one compound of formula I wherein the compound is a transition metal ion chelate of iron.

In one embodiment, a composition includes at least one compound of formula II, a salt thereof, or chelate thereof, wherein each $R^3$ is independently selected from hydrogen, —($C_2$-$C_{16}$)alkyl, —($C_2$-$C_{16}$)alkenyl, -mannitosyl, -sorbitolyl, or -sucrosyl; wherein at least one of $R^3$ is not hydrogen. In another embodiment, a composition include at least one compound of formula II, wherein each $R^3$ is independently selected from hydrogen,

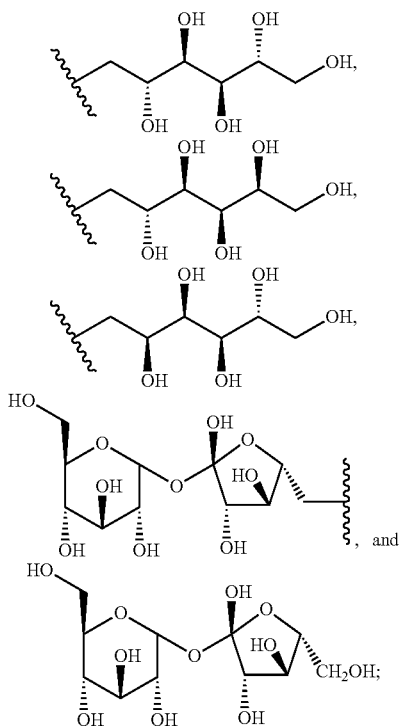

wherein at least one $R^3$ is not hydrogen.

In still another embodiment, a composition includes at least one compound of formula II, each $R^3$ is independently selected from hydrogen,

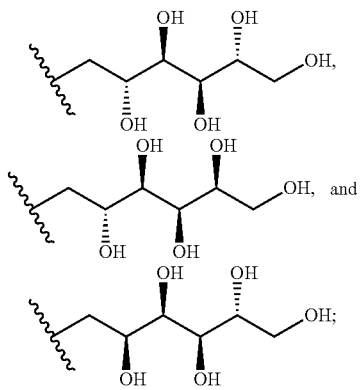

and wherein at least one $R^3$ is not hydrogen. In yet another embodiment, a composition includes at least one compound of formula II, each $R^3$ is independently selected from hydrogen, —($C_2$-$C_{16}$)alkyl, —($C_2$-$C_{16}$)alkenyl; and wherein at least one $R^3$ is not hydrogen. In another embodiment, each $R^3$ is independently selected from —($C_2$-$C_{16}$)alkyl, and —($C_2$-$C_{16}$)alkenyl. In another embodiment, at least two of $R^3$ are not hydrogen. In still another embodiment, at least three of $R^3$ are not hydrogen. In yet another embodiment, at least four of $R^3$ are not hydrogen. In some embodiments, all $R^3$ in chemical structure (II) are not hydrogen. In each of the various embodiments, alkyl or alkenyl may be substituted with an amino acid or a sugar such as, for example, mannitosyl, sorbitolyl, or sucrosyl.

In one embodiment, the compositions disclosed herein may include at least one compound of formula II wherein the compound is a sodium salt, ammonium salt, potassium salt, calcium salt, magnesium salt, manganese salt, zinc salt, iron salt, or a combination thereof. In one embodiment, the compositions disclosed herein may include at least one compound of formula II wherein the compound is a transition metal ion chelate of iron.

In one embodiment, a composition includes at least one compound of formula III, a salt thereof, or chelate thereof, wherein each $R^4$ is independently selected from hydrogen, —(C=O)—($C_8$-$C_{16}$)alkyl, —(C=O)—($C_8$-$C_{16}$)alkenyl, wherein at least one $R^4$ is not hydrogen. Another embodiment provides a composition including at least one compound of formula III, wherein at least one $R^4$ on each ring B, C, D, E and F is not hydrogen. Still another embodiment provides a composition including at least one compound of formula III, wherein at least five $R^4$ are not hydrogen. Yet another embodiment provides a composition, including at least one compound of formula III, wherein at least ten $R^4$ are not hydrogen. In the various embodiments, the compound of formula III may be unsymmetrically substituted.

In one embodiment, the compositions disclosed herein may include at least one compound of formula III wherein the compound is a sodium salt, ammonium salt, potassium salt, calcium salt, magnesium salt, manganese salt, zinc salt, iron salt, or a combination thereof. In one embodiment, the compositions disclosed herein may include at least one compound of formula III wherein the compound is a transition metal ion chelate of iron.

A method of preparing a plasticizing compound as described above includes esterifying at least one of gallic acid, fulvic acid, and tannic acid to form at least one plasticizing compound, respectively of formula I, formula II, or formula III, a salt thereof, a chelate thereof, or a combination thereof, wherein at least one of $R^{1A}$, $R^{1B}$, $R^{1C}$, and $R^2$ are not hydrogen; each $R^3$ is independently selected from hydrogen, —($C_2$-$C_{16}$)alkyl, —($C_2$-$C_{16}$)alkenyl, -mannitosyl, -sorbitolyl, or -sucrosyl; wherein at least one of $R^3$ is not hydrogen; and each $R^4$ is independently selected from hydrogen, —(C=O)—($C_8$-$C_{16}$)alkyl, and —(C=O)—($C_8$-$C_{16}$)alkenyl, each $R^4$ may be the same or different, wherein at least one of $R^4$ is not hydrogen.

In an embodiment, the method includes esterifying gallic acid to form at least one plasticizing compound of formula I, wherein $R^{1A}$, $R^{1B}$, and $R^{1C}$ are independently selected from hydrogen, —(C=O)—($C_8$-$C_{16}$)alkyl, and —(C=O)—($C_8$-$C_{16}$)alkenyl; $R^2$ is hydrogen, —($C_8$-$C_{16}$)alkyl, —($C_8$-$C_{16}$)alkenyl, -mannitosyl, -sorbitolyl, or -sucrosyl, and wherein at least one of $R^{1A}$, $R^{1B}$, $R^{1C}$, and $R^2$ are not hydrogen.

Another embodiment includes esterifying gallic acid to form at least one plasticizing compound of formula I, wherein $R^{1A}$, $R^{1B}$, and $R^{1C}$ are independently selected from hydrogen, —(C=O)—($C_8$-$C_{16}$)alkyl, or —(C=O)—($C_8$-$C_{16}$)alkenyl; having $R^2$ is —($C_8$-$C_{16}$)alkyl, or —($C_8$-$C_{16}$)alkenyl; and wherein at least one of $R^{1A}$, $R^{1B}$, and $R^{1C}$ is not hydrogen. In still another embodiment, the method includes esterifying gallic acid to form at least one compound of formula I, wherein $R^{1A}$, $R^{1B}$, and $R^{1C}$ are independently selected from hydrogen, —(C=O)—($C_8$-$C_{16}$)alkyl, or —(C=O)—($C_8$-$C_{16}$)alkenyl, $R^2$ is -mannitosyl, -sorbitolyl, or -sucrosyl; and wherein at least one of $R^{1A}$, $R^{1B}$, and $R^{1C}$ is not hydrogen. In yet another embodiment, the method includes esterifying gallic acid to form at least one compound of formula I, wherein $R^{1A}$, $R^{1B}$, and $R^{1C}$ are independently selected from hydrogen, —(C=O)—($C_8$-$C_{16}$)alkyl, or —(C=O)—($C_8$-$C_{16}$)alkenyl, $R^2$ is selected from:

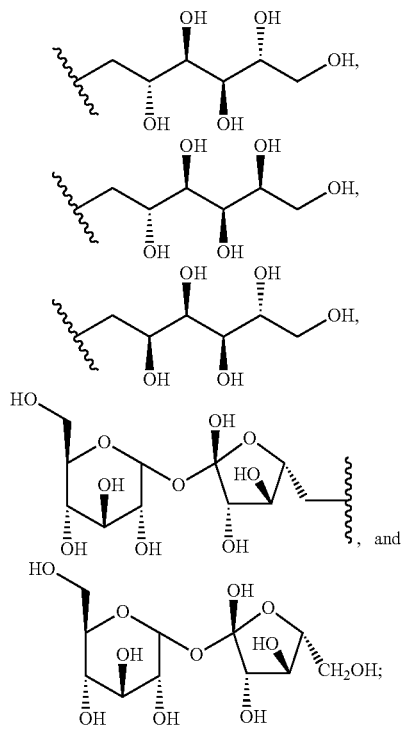

and
wherein at least one of $R^{1A}$, $R^{1B}$, and $R^{1C}$ is not hydrogen.

In still another embodiment, the method includes esterifying gallic acid to form at least one compound of formula I, wherein $R^{1A}$, $R^{1B}$, and $R^{1C}$ are independently selected from hydrogen, —(C=O)—($C_8$-$C_{16}$)alkyl, or —(C=O)—($C_8$-$C_{16}$)alkenyl, $R^2$ is selected from

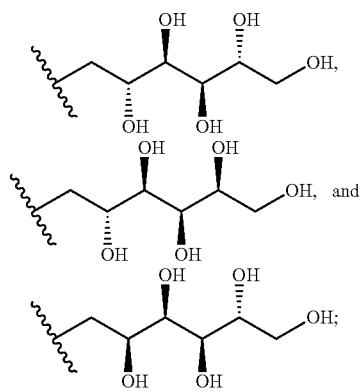

and wherein at least one of $R^{1A}$, $R^{1B}$, and $R^{1C}$ is not hydrogen. In another embodiment, $R^{1A}$, $R^{1B}$ and $R^{1C}$ are independently selected from —(C=O)—($C_8$-$C_{16}$)alkyl, and —(C=O)—($C_8$-$C_{16}$)alkenyl, $R^2$ is hydrogen, —($C_8$-$C_{16}$)alkyl, —($C_8$-$C_{16}$)alkenyl, -mannitosyl, -sorbitolyl, or -sucrosyl. In another embodiment, $R^{1A}$, $R^{1B}$, and $R^{1C}$ are independently selected from —(C=O)—($C_8$-$C_{16}$)alkyl, and —(C=O)—($C_8$-$C_{16}$)alkenyl, $R^2$ is —($C_8$-$C_{16}$)alkyl, —($C_8$-$C_{16}$)alkenyl, -mannitosyl, -sorbitolyl, or -sucrosyl methods.

In an embodiment, the method may include esterifying gallic acid to form at least one compound of formula I wherein the compound is a salt thereof, or chelate thereof. In an embodiment, the method may include esterifying gallic acid to form at least one compound of formula I wherein the compound is a sodium salt, ammonium salt, potassium salt, calcium salt, magnesium salt, manganese salt, zinc salt, iron salt, or a combination thereof. In an embodiment, the method may include esterifying gallic acid to form at least one compound of formula I wherein the compound is a transition metal ion chelate.

In an embodiment, the method includes esterifying fulvic acid to form at least one plasticizing compound of formula II, a salt thereof, or chelate thereof; wherein each $R^3$ is independently selected from hydrogen, —($C_2$-$C_{16}$)alkyl, —($C_2$-$C_{16}$)alkenyl, -mannitosyl, -sorbitolyl, and -sucrosyl; wherein at least one of $R^3$ is not hydrogen.

In one embodiment, the method includes esterifying fulvic acid to form at least one compound of formula II, a salt thereof, or chelate thereof, wherein each $R^3$ is independently selected from hydrogen, —($C_2$-$C_{16}$)alkyl, —($C_2$-$C_{16}$)alkenyl, -mannitosyl, -sorbitolyl, or -sucrosyl; wherein at least one $R^3$ is not hydrogen. In another embodiment, the method includes esterifying fulvic acid to form at least one compound of formula II, wherein each $R^3$ is independently selected from hydrogen,

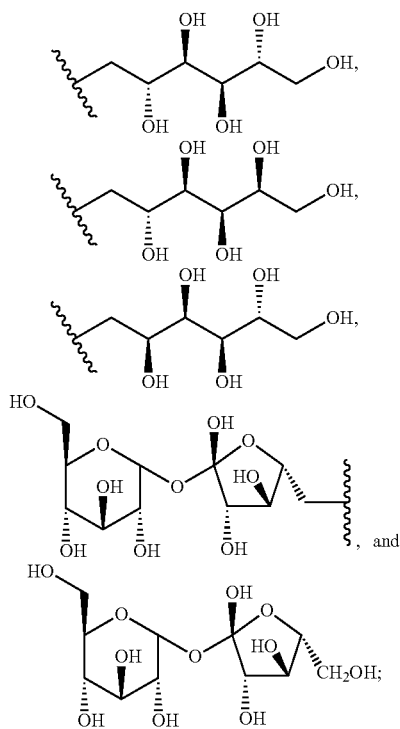

wherein at least one $R^3$ is not hydrogen.

In still another embodiment, the method includes esterifying fulvic acid to form at least one compound of formula II, wherein each $R^3$ is independently selected from hydrogen,

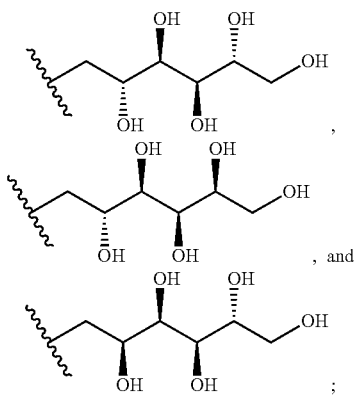

and wherein at least one $R^3$ is not hydrogen. In yet another embodiment, the method includes esterifying fulvic acid to form at least one compound of formula II, wherein each $R^3$ is independently selected from hydrogen, —($C_2$-$C_{16}$)alkyl, —($C_2$-$C_{16}$)alkenyl; and wherein at least one $R^3$ is not hydrogen. In another embodiment, each $R^3$ is independently selected from —($C_2$-$C_{16}$)alkyl, and —($C_2$-$C_{16}$)alkenyl. In another embodiment, at least two $R^3$ are not hydrogen. In still another embodiment, at least three $R^3$ are not hydrogen. In yet another embodiment, at least four of $R^3$ are not hydrogen. In still another embodiment, none of $R^3$ are hydrogen. In each of the various embodiments, alkyl or alkenyl may be substituted with a sugar, for example mannitosyl, sorbitolyl, or sucrosyl, or with an amino acid.

In one embodiment, the methods may include esterifying fulvic acid to form at least one compound of formula II wherein the compound is a sodium salt, ammonium salt, potassium salt, calcium salt, magnesium salt, manganese salt, zinc salt, iron salt, or a combination thereof. In one embodiment, the methods may include esterifying fulvic acid to form at least one compound of formula II wherein the compound is a transition metal ion chelate of iron.

In one embodiment, the method includes esterifying tannic acid to form at least one compound of formula III, a salt thereof, or chelate thereof, and wherein each $R^4$ is independently selected from hydrogen, —(C=O)—($C_8$-$C_{16}$)alkyl, and —(C=O)—($C_8$-$C_{16}$)alkenyl, wherein at least one $R^4$ is not hydrogen. In another embodiment, the method includes esterifying tannic acid to form at least one compound of formula III, wherein at least one $R^4$ on each ring B, C, D, E and F are not hydrogen. In still another embodiment, the method includes esterifying tannic acid to form at least one compound of formula III, wherein at least five $R^4$ are not hydrogen. In yet another embodiment, the method includes esterifying tannic acid to form at least one compound of formula III, wherein at least ten $R^4$ are not hydrogen. In still another embodiment, none of the $R^4$ are hydrogen. In each of the various embodiments, alkyl or alkenyl may be substituted with a sugar, for example mannitosyl, sorbitolyl, or sucrosyl, or with an amino acid.

In one embodiment, the methods may include esterifying tannic acid to form at least one compound of formula III wherein the compound is a sodium salt, ammonium salt, potassium salt, calcium salt, magnesium salt, manganese salt, zinc salt, iron salt, or a combination thereof. In one embodiment, the methods may include esterifying tannic acid to form at least one compound of formula III wherein the compound is a transition metal ion chelate.

Disclosed is a treated food product including at least one plasticizing compound of formula I, formula II, or formula III, or a salt thereof, or chelate thereof, wherein $R^{1A}$, $R^{1B}$, and $R^{1C}$ are independently selected from hydrogen, —(C═O)—($C_8$-$C_{16}$)alkyl, and —(C═O)—($C_8$-$C_{16}$)alkenyl; $R^2$ is hydrogen, —($C_8$-$C_{16}$)alkyl, —($C_8$-$C_{16}$)alkenyl, -mannitosyl, -sorbitolyl, or -sucrosyl; wherein at least one of $R^{1A}$, $R^{1B}$, $R^{1C}$, and $R^2$ are not hydrogen; each $R^3$ is independently selected from hydrogen, —($C_2$-$C_{16}$)alkyl, —($C_2$-$C_{16}$)alkenyl, -mannitosyl, -sorbitolyl, and -sucrosyl; wherein at least one of $R^3$ is not hydrogen; and each $R^4$ is independently selected from hydrogen, —(C═O)—($C_8$-$C_{14}$)alkyl, and —(C═O)—($C_8$-$C_{14}$)alkenyl, wherein at least one $R^4$ on each ring B, C, D, E, and F is not hydrogen; in a food product. In still another embodiment, none of the $R^{1A}$, $R^{1B}$, $R^{1C}$, $R^2$, $R^3$, or $R^4$ groups of the compounds are hydrogen. In each of the various embodiments, alkyl or alkenyl may be substituted with a sugar, for example mannitosyl, sorbitolyl, or sucrosyl, or with an amino acid.

In one embodiment, the food product includes a dairy product, fat, oil, fat emulsion, edible ice, fruit, vegetable, fungi, seaweed, nuts, seeds, confectionery, cereal, cereal product derived from cereal grains, bakery ware, meat, meat byproduct, fish, fish product, egg product, sugar, artificial sweetener, spices, condiment, soup, sauce, salad, protein mix, non-dairy beverage, savory snack, or combinations thereof. In another embodiment, the food product includes a vegetable oil, animal fat, processed cheeses, chewing gum base, processed meat products, dried meats, sausages, beef patties, meatballs, frozen seafood, pizza toppings, protein, yeast, bakery products, dry cereals, spices, dehydrated potatoes, potato chips, beverage mixes, nonalcoholic beverages, mixed nuts, fruit, vegetables, butter, margarine, dairy products, breakfast bar, baby food, pasta, pet food, fish food, or combinations thereof.

In another embodiment, the plasticizing compound includes at least two compounds of formula I, formula II, formula III, a salt thereof, or chelate thereof, wherein $R^{1A}$, $R^{1B}$, and $R^{1C}$ are independently selected from hydrogen, —(C═O)—($C_8$-$C_{16}$)alkyl, and —(C═O)—($C_8$-$C_{16}$)alkenyl; $R^2$ is hydrogen, —($C_8$-$C_{16}$)alkyl, —($C_8$-$C_{16}$)alkenyl, -mannitosyl, -sorbitolyl, or -sucrosyl; wherein at least two of $R^{1A}$, $R^{1B}$, $R^{1C}$, and $R^2$ are not hydrogen; each $R^3$ is independently selected from hydrogen, —($C_2$-$C_{16}$)alkyl, —($C_2$-$C_{16}$)alkenyl, -mannitosyl, -sorbitolyl, and -sucrosyl; wherein at least one of $R^3$ is not hydrogen; and each $R^4$ is independently selected from hydrogen, —(C═O)—($C_8$-$C_{16}$)alkyl, and —(C═O)—($C_8$-$C_{16}$)alkenyl, wherein at least one of $R^4$ on each ring B, C, D, E, and F is not hydrogen. In yet another embodiment, the plasticizing compound is a compound of formula I, formula II, formula III, a salt thereof, or chelate thereof. In still another embodiment, none of the $R^{1A}$, $R^{1B}$, $R^{1C}$, $R^2$, $R^3$, or $R^4$ groups of the compounds are hydrogen. In each of the various embodiments, alkyl or alkenyl may be substituted with a sugar, for example mannitosyl, sorbitolyl, or sucrosyl, or with an amino acid.

A method of preparing a treated food product includes adding at least one plasticizing compound of formula I, formula II, formula III, a salt thereof, or chelate thereof, wherein $R^{1A}$, $R^{1B}$, and $R^{1C}$ are independently selected from hydrogen, —(C═O)—($C_8$-$C_{16}$)alkyl, and —(C═O)—($C_8$-$C_{16}$)alkenyl, $R^2$ is hydrogen, —($C_8$-$C_{16}$)alkyl, —($C_8$-$C_{16}$)alkenyl, -mannitosyl, -sorbitolyl, or -sucrosyl, wherein at least two of $R^{1A}$, $R^{1B}$, $R^{1C}$, and $R^2$ are not hydrogen; each $R^3$ is independently selected from hydrogen, —($C_2$-$C_{16}$)alkyl, ($C_2$-$C_{16}$)alkenyl, -mannitosyl, -sorbitolyl, and -sucrosyl; wherein at least one of $R^3$ is not hydrogen; and each $R^4$ is independently selected from hydrogen, —(C═O)—($C_8$-$C_{16}$)alkyl, and —(C═O)—($C_8$-$C_{16}$)alkenyl, each $R^4$ may be the same or different; wherein at least one $R^4$ on each ring B, C, D, E, and F is not hydrogen; to a food product. In still another embodiment, none of the $R^{1A}$, $R^{1B}$, $R^{1C}$, $R^2$, $R^3$, or $R^4$ groups of the compounds are hydrogen. In each of the various embodiments, alkyl or alkenyl may be substituted with a sugar, for example mannitosyl, sorbitolyl, or sucrosyl, or with an amino acid. In some embodiments, the plasticizing compound has formula I, formula II, formula III, a salt thereof, or a chelate thereof.

In an embodiment, the plasticizing compound extends the shelf-life of the food product. In another embodiment, the treated food product is stable at temperatures up to about 300° C. In still yet another embodiment, the plasticizing compound includes at least one compound of formula I, formula II, formula III, a salt thereof, or chelate thereof.

In various embodiments, the plasticizer compound is present in the food product at a concentration of about 0.05% to about 5% by weight (w/w). In an embodiment, the plasticizing compound is present in the food product at a concentration of about 0.1% to about 0.2% by weight (w/w). In an embodiment, the plasticizer compound is present in the food product at a concentration, by weight, of about 5%, about 2.5%, about 1%, about 0.5%, about 0.1%, about 0.05% or any range between two of the concentrations.

The plasticizer compounds described herein have various uses including as plasticizers for several edible polymeric systems and food packaging materials such as gelatin, polysaccharides, starch, cellulosic derivatives polyvinyl acetate, cellulose acetate and polyvinyl chloride (PVC). These disclosed compositions can be used as a viscous liquids, a solution, or chelation with transition (nutrient) metals. In one embodiment, a polymeric matrix includes at least one plasticizing compound of formula I, II, or III, a salt thereof, or chelate thereof, in combination with an edible polymer such as gelatin, polysaccharides, starch, cellulosic derivatives, or combination thereof. In yet other embodiments, the polymeric matrix may be suitable for various packaging materials such as polyvinyl acetate, cellulose acetate, and polyvinyl chloride to improve their properties and to extend a shelf life of a product. In certain embodiments, the polymeric matrix is a food packaging, pharmaceutical packaging or personal care packaging that are compatible with these natural based plasticizers.

In various specific embodiments, the plasticizer compound is present in a polymeric matrix used in packaging at a concentration of less than about 20% by weight (w/w), less than about 10% by weight (w/w), less than about 5% by weight (w/w), less than about 2% by weight (w/w), less than about 1% by weight (w/w), or less than about 0.5% by weight (w/w), or in any combination between them.

In an embodiment, the compositions disclosed herein may be incorporated into personal care products such as cosmetics. In an embodiment, the cosmetics may include a lip balm, lip gloss, lipstick, lip stains, lip tint, blush, bronzers, highlighters, concealers, neutralizers, foundations, foundation primer, glimmers, shimmers, powders, eye shadow, eye color, eye liner, mascara, nail polish, nail treatments-strengtheners, make-up, body creams, moisturizers, suntan preparations, sunless tan formulations, body butter, body scrubs, make-up remover, shampoos, conditioners, dandruff control formulations, anti-frizz formulations, straightening formulations, volumizing formulations, styling aids, hairsprays, hair gels, hair colors and tinting formulations, anti-aging creams, body gels, essential oils, creams, cleansers, soap, or combinations thereof.

EXAMPLES

Although the present technology has been described in considerable detail with reference to certain preferred embodiments thereof, other versions are possible. Therefore the spirit and scope of the appended claims should not be limited to the description and the preferred versions contained within this specification. Various aspects of the present technology will be illustrated with reference to the following non-limiting examples.

Example 1: Preparation of Gallic Acid Tridecanoate

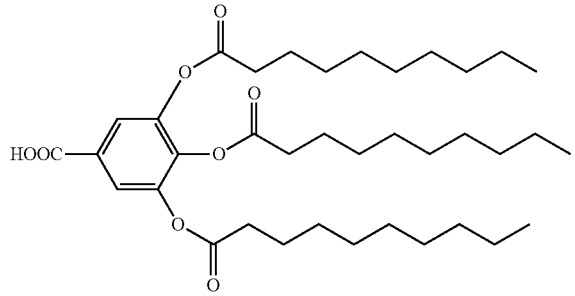 [SMILES: CCCCCCCCCC(=O)Oc1cc(C(=O)O)cc(OC(=O)CCCCCCCCC)c1OC(=O)CCCCCCCCC]

Decanoic acid (133.5 grams, 0.75 moles), gallic acid (43 grams, 0.25 moles) and anhydrous phosphoric acid (5 grams) are charged to a four-necked, 500-mL round-bottom flask fitted with a nitrogen sparge leg, thermometer, magnetic stirrer, and a rectifying column. The flask is heated at about 80° C. to melt the caproic acid. The gallic acid is suspended in the melt under a subtle nitrogen sparge with constant agitation. Water from the reaction is liberated throughout the reaction and is removed via the rectifying column continuously. The reaction is terminated after 16 hours by stopping the heat input and cooling. The unreacted acid is extracted with 10% sodium carbonate. The viscous gallic ester is washed with water and dried under vacuum, and analyzed. The yield of the gallic ester derivatives is 75% based on gallic acid reactive material.

Example 2: Preparation of Decyl Fulvate Plasticizer

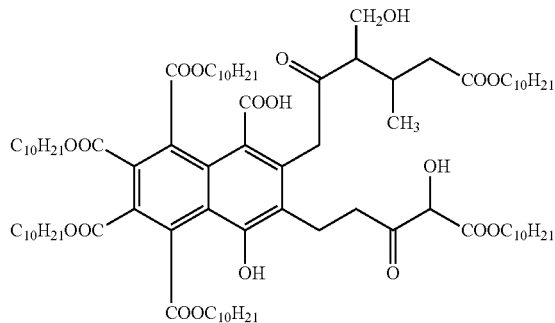

The set-up of example 1 is used. The reaction vessel is charged with decanol (1 mol, 158 grams). Solid fulvic acid (Formula II, $R^3$=H, 63.8 grams) is added (0.1 mol) and then 3 grams of hydrochloric acid. The mixture is heated to 80° C. After completion of the reaction. The product is poured into 250 grams of boiling water with mixing. The unreacted decanol is soluble in boiled water. The oily layer is separated from the aqueous layer and then dried under vacuum. The unreacted decanol can be separated from water and re-used.

Example 3: Preparation of Penta-Nonoyl Ester of Tannic Acid

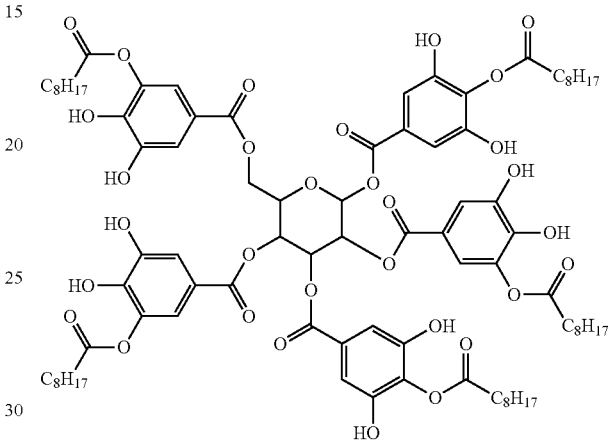

The set-up of example 1 is used. The reaction vessel is charged with nonanoic acid (267 grams, 1.5 moles), tannic acid (141 grams, 0.15 moles) and ortho-phosphorous acid (anhydrous) (5 grams). The flask is fitted with a nitrogen sparge leg, thermometer, magnetic stirrer, and a rectifying column. The flask is heated at about 80° C. under a nitrogen sparge with constant agitation. As the reaction proceeds the tannic acid is transformed gradually to its ester derivative. Water from the reaction is liberated throughout the reaction and is removed via the rectifying column continuously. The reaction is terminated after 16 hours by stopping the heat input and then cooling.

The unreacted nonanoic acid is extracted with 10% sodium carbonate. The viscous semisolid tannic ester is washed with water and dried under vacuum, and then analyzed. The yield of the gallic ester derivatives is 85% based on tannic acid reactive material.

Example 4: Gallic Acid Derivatives as Plasticizers for Chewing Gum

Warm beeswax (28 grams) is mixed with warm chicle (170 grams) and 4.5 grams of the food plasticizer of Example 1 to make a gum base. To the warmed gum base is mixed powdered sugar (5 grams). The gum base/powdered sugar mixture is spread into the desired shape, dusted with powdered sugar, and cooled to form chewing gum. The chewing gum has an enhanced nutritional value due to the antioxidant properties of the food plasticizer.

Example 5: Fulvic Acid Derivatives as Plasticizers for Snack Bars

A snack bar is prepared by mixing 1 Kg chopped peanuts, 1 Kg chopped cashews, 500 grams raisins, 500 grams chocolate bits, 250 grams flaked coconut, and 100 grams of the food plasticizer of Example 2, and then pressing into the desired shape. The snack bars have an enhanced nutritional value due to the antioxidant properties of the food plasticizer.

Example 6: Plasticization of Cosmetic

Stearic acid (2.7 wt %), palmitic acid (2.7 wt %), 1-hexadecanol (5.4 wt %), 1-octadecanol (2.7 wt %), sorbitan monostearate (3.1 wt %), triton X-100 (18 wt %), carbomer (0.5 wt %) and the food plasticizer of Example 3 (5 wt %) are heated at 70° C. with constant stirring for an hour. Distilled water (60 wt %), is then poured into the organic phase of the mixture and homogenized for 15 minutes at the same temperature. The stabilized cosmetics have greater stability, better rheological properties with less discoloration compared to the non-plasticized cosmetics.

Example 7: Plasticization of Polyvinyl Acetate for Food Packaging

Polyvinyl acetate containing 5% by weight of the plasticizer of Example 1 is extruded to form films for food packaging. The films are subjected to natural sun light and with high UV light for 4 weeks. The resultant films are tested by IR and UV spectrometry. The films show no color change and no spectral changes while polyvinyl acetate without the plasticizer as controls show poor film forming properties.

Example 8: Plasticization and Stabilization of Polyvinyl Chloride (PVC) for Food Packaging Polyvinylchloride (K value=70) is stabilized with 5% by weight of the plasticizer of Example 2 in the form of a metal chelate and 5% plasticizer in the form of ester is compounded by rheometer, then extruded to form films for food packaging. The film shows good mechanical properties. The films are subjected to natural sunlight and with high UV light for 4 weeks. The plasticized and stabilized films shows no color change while control films of commercial polyvinyl chloride samples without stabilizers show change in coloration to a dark yellowish color with brittle behavior.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

While various compositions and methods are described in terms of "comprising" various components or steps (interpreted as meaning "including, but not limited to"), the compositions and methods can also "consist essentially of" or "consist of" the various components and steps, and such terminology should be interpreted as defining essentially closed-member groups.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," and the like). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, and the like" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, and the like). In those instances where a convention analogous to "at least one of A, B, or C, and the like" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, and the like). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or embodiments of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, and the like. As a non-limiting example, each range discussed herein can be readily broken down into a lower third, middle third and upper third, and the like. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

The term "alkyl" or "alkyl group" refers to a branched or unbranched hydrocarbon or group of 2 to 20 carbon atoms, unless otherwise specified, such as but not limited to ethyl, n-propyl, isopropyl, n-butyl, isobutyl, t-butyl, octyl, decyl, tetradecyl, hexadecyl, eicosyl, tetracosyl and the like. The term "alkenyl" or "alkenyl group" refers to a branched or unbranched hydrocarbon or group of 2 to 20 carbon atoms, unless otherwise specified, having one or more unsaturations, such as but not limited to ethenyl, propenyl, butenyl, butadienyl, isobutylenyl, and the like. Alkyl groups and alkenyl groups may be substituted with sugars or amino acids. Substitution by sugars may include, but is not limited to, substitution by mannitosyl, sorbitolyl, or sucrosyl. Substitution by amino acid may include substitution by any of the twenty common amino acids.

As used herein, the term "rheometer" shall mean rheometers, viscometers, viscosimeters and similar instruments that are used to measure the properties of fluid or similar materials. Rheological properties can affect the design of food processing plants, shelf life, and product sensory properties.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A plasticizing composition comprising a compound of formula I:

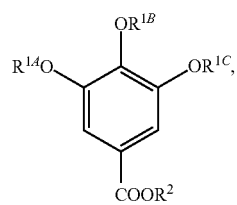

a salt thereof, a chelate thereof, or a combination thereof, wherein $R^{1A}$, $R^{1B}$, and $R^{1C}$ are independently selected from hydrogen, —(C=O)—($C_8$-$C_{16}$)alkyl, or —(C=O)—($C_8$-$C_{16}$)alkenyl, wherein at least two of $R^{1A}$, $R^{1B}$, and $R^{1C}$ are not hydrogen;

$R^2$ is —($C_8$-$C_{16}$)alkyl, —($C_8$-$C_{16}$)alkenyl, -mannitosyl, -sorbitolyl, or -sucrosyl.

2. The composition of claim 1, wherein $R^2$ is —($C_8$-$C_{16}$)alkyl or —($C_8$-$C_{16}$)alkenyl.

3. The composition of claim 1, wherein $R^2$ is -mannitosyl, -sorbitolyl, or -sucrosyl.

4. The composition of claim 1, wherein $R^2$ is selected from the group consisting of:

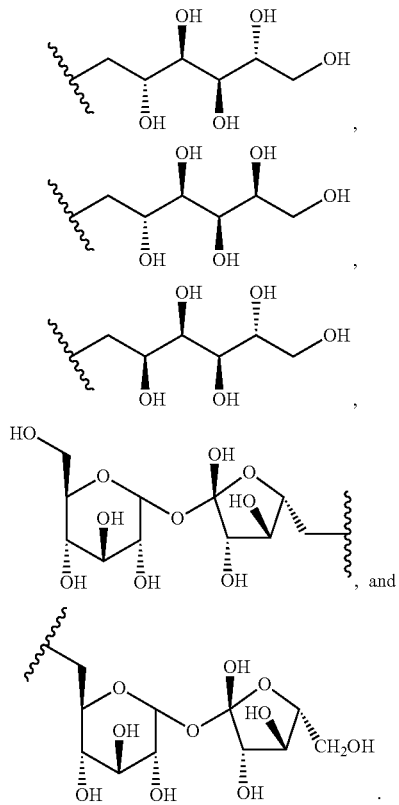

5. The composition of claim 1, wherein $R^2$ is selected from the group consisting of:

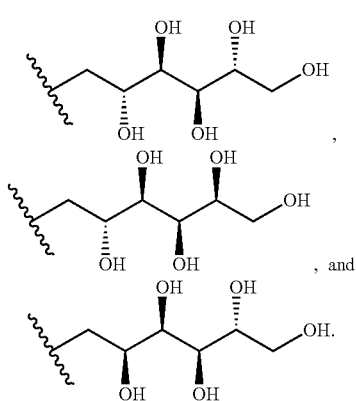
, and

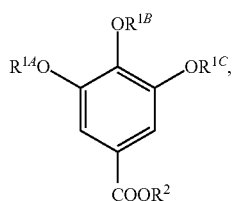

6. The composition of claim 1, wherein $R^{1A}$, $R^{1B}$, and $R^{1C}$ are independently selected from —(C=O)—(C$_8$-C$_{16}$)alkyl and —(C=O)—(C$_8$-C$_{16}$)alkenyl.

7. The composition of claim 1, wherein the at least one compound comprises a sodium salt, an ammonium salt, a potassium salt, a calcium salt, a magnesium salt, a manganese salt, a zinc salt, an iron salt, or a combination thereof.

8. The composition of claim 1, wherein the at least one compound comprises a transition metal ion chelate.

9. A method of preparing a plasticizing compound, the method comprising esterifying gallic acid to form a plasticizing compound of formula I:

$$R^{1A}O \overset{OR^{1B}}{\underset{COOR^2}{\text{—}}} OR^{1C},$$

I a salt thereof, a chelate thereof, or a combination thereof, wherein $R^{1A}$, $R^{1B}$, and $R^{1C}$ are independently selected from hydrogen, —(C=O)—(C$_8$-C$_{16}$)alkyl, and —(C=O)—(C$_8$-C$_{16}$)alkenyl, wherein at least two of $R^{1A}$, $R^{1B}$, and $R^{1C}$ are not hydrogen;
$R^2$ is —(C$_8$-C$_{16}$)alkyl, —(C$_8$-C$_{16}$)alkenyl, -mannitosyl, -sorbitolyl, or -sucrosyl.

10. The method of claim 9, wherein the method includes esterifying the gallic acid to form at least one compound of formula I, wherein $R^{1A}$, $R^{1B}$, and $R^{1C}$ are independently selected from hydrogen, —(C=O)—(C$_8$-C$_{16}$)alkyl, and —(C=O)—(C$_8$-C$_{16}$)alkenyl, wherein at least two of $R^{1A}$, $R^{1B}$, and $R^{1C}$ are not hydrogen;
wherein $R^2$ is selected from the group consisting of:

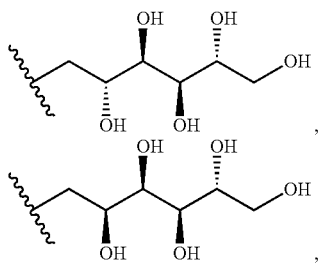

-continued
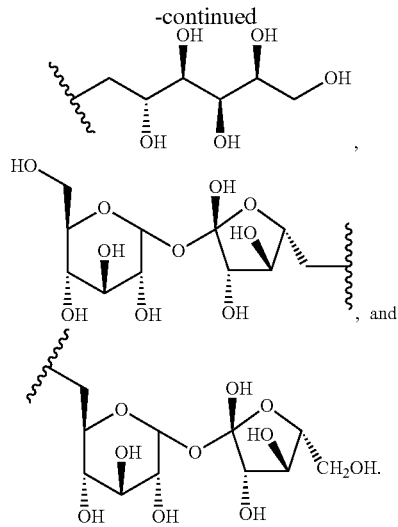

11. The method of claim 9, wherein the method includes esterifying the gallic acid to form at least one compound of formula I, wherein $R^2$ is selected from the group consisting of

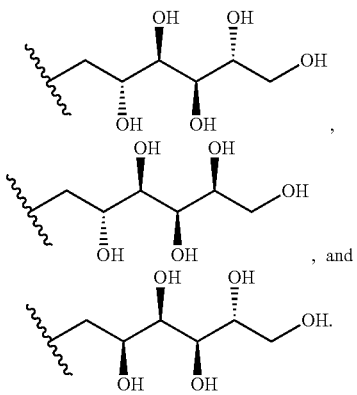

12. The method of claim 9, wherein $R^{1A}$, $R^{1B}$, and $R^{1C}$ are independently selected from —(C=O)—(C$_8$-C$_{16}$)alkyl and —(C=O)—(C$_8$-C$_{16}$)alkenyl.

13. The method of claim 9, wherein the method comprises esterifying the gallic acid to form at least one compound of formula I, wherein the compound is a sodium salt, an ammonium salt, a potassium salt, a calcium salt, a magnesium salt, a manganese salt, a zinc salt, an iron salt, or a combination thereof.

14. The method of claim 9, wherein the method comprises esterifying the gallic acid to form at least one compound of formula I, wherein the compound is a transition metal ion chelate.

15. A treated food product comprising at least one of the plasticizing compound of formula I of claim 1, wherein the food product comprises a dairy product, fat, oil, fat emulsion, edible ice, fruit, vegetable, fungi, seaweed, nuts, seeds, confectionery, cereal, cereal product derived from cereal grains, bakery ware, meat, meat byproduct, fish, fish product, egg product, sugar, artificial sweetener, spices, condiment, soup, sauce, salad, protein mix, non-dairy beverage, savory snack, or combinations thereof.

* * * * *